(12) United States Patent
Kronholm et al.

(10) Patent No.: US 7,825,161 B2
(45) Date of Patent: *Nov. 2, 2010

(54) HIGHER FULLERENES USEFUL AS RADICAL SCAVENGERS

(75) Inventors: David F. Kronholm, Boston, MA (US); Jan C. Hummelen, Groningen (NL); Alexander B. Sieval, Groningen (NL)

(73) Assignee: Nano-C, Inc., Westwood, MA (US)

( * ) Notice: Subject to any disclaimer, the term of this patent is extended or adjusted under 35 U.S.C. 154(b) by 893 days.

This patent is subject to a terminal disclaimer.

(21) Appl. No.: 11/014,207

(22) Filed: Dec. 15, 2004

(65) Prior Publication Data

US 2005/0239717 A1    Oct. 27, 2005

Related U.S. Application Data

(60) Provisional application No. 60/529,988, filed on Dec. 15, 2003.

(51) Int. Cl.
*A01N 37/00* (2006.01)
*A01N 25/00* (2006.01)

(52) U.S. Cl. ..................... 514/577; 514/789
(58) Field of Classification Search ........... None
See application file for complete search history.

(56) References Cited

U.S. PATENT DOCUMENTS

| | | | |
|---|---|---|---|
| 3,242,144 A | 3/1966 | McNally | |
| 5,462,680 A * | 10/1995 | Brois et al. | 508/110 |
| 5,648,523 A | 7/1997 | Chiang | |
| 5,739,376 A | 4/1998 | Bingel et al. | |
| 5,994,410 A | 11/1999 | Chiang et al. | |
| 6,020,523 A | 2/2000 | Chiang | |
| 6,046,361 A | 4/2000 | Chiang | |
| 6,265,443 B1 | 7/2001 | Choi et al. | |
| 6,380,434 B1 | 4/2002 | Chiang | |
| 6,399,785 B1 | 6/2002 | Murphy et al. | |
| 6,455,709 B1 | 9/2002 | Chiang et al. | |
| 6,576,655 B2 | 6/2003 | Chiang et al. | |
| 6,593,137 B1 | 7/2003 | Erlanger et al. | |
| 6,660,248 B2 | 12/2003 | Wilson et al. | |
| 6,790,963 B2 | 9/2004 | Chiang et al. | |

(Continued)

FOREIGN PATENT DOCUMENTS

DE    4433245    3/1966

(Continued)

OTHER PUBLICATIONS

European Search Report, EP 04814500.7.

(Continued)

*Primary Examiner*—Karl J Puttlitz
(74) *Attorney, Agent, or Firm*—Wilmer Cutler Pickering Hale and Dorr LLP

(57) ABSTRACT

Chemically functionalized fullerenes are useful in various applications as radical scavengers. These chemically functionalized fullerenes offer the advantages of preservation of the high innate radical scavenging efficiency of the fullerene cage and ease of synthesis of fullerene derivatives of desirably altered chemical and physical properties and single isomers. Further, they are based on a common intermediate chemistry and intermediates can be easily functionalized and tailored to various requirements.

26 Claims, 8 Drawing Sheets

1

U.S. PATENT DOCUMENTS

| | | | |
|---|---|---|---|
| 2001/0041801 | A1 | 11/2001 | Friedman et al. |
| 2003/0065206 | A1 | 4/2003 | Bolskar et al. |
| 2003/0113940 | A1 | 6/2003 | Erlanger et al. |
| 2003/0162837 | A1 | 8/2003 | Dugan et al. |
| 2004/0028597 | A1 | 2/2004 | Waiblinger et al. |
| 2004/0166152 | A1 | 8/2004 | Hirsch et al. |
| 2005/0143327 | A1* | 6/2005 | Hirsch .................. 514/33 |
| 2005/0191229 | A1* | 9/2005 | Chiang et al. .......... 423/445 B |
| 2005/0245606 | A1 | 11/2005 | Kronholm et al. |
| 2006/0159611 | A1 | 7/2006 | Hummelen et al. |
| 2009/0197951 | A1* | 8/2009 | Lebovitz et al. ............ 514/547 |

FOREIGN PATENT DOCUMENTS

| | | |
|---|---|---|
| EP | 0647606 | 10/1994 |
| JP | 07-188129 | 7/1995 |
| JP | 2004/269523 | 9/2004 |
| JP | 2005053832 | 3/2005 |
| WO | WO 9609275 | 3/1996 |
| WO | WO 97/03975 | 2/1997 |
| WO | 98/32863 * | 7/1998 |
| WO | WO 99/43358 | 9/1999 |
| WO | WO 03/072802 A2 | 9/2003 |
| WO | WO 2004/073082 A1 | 2/2004 |

OTHER PUBLICATIONS

Chi, Y. et al., Novel Water-soluble Hexa (sulfobutyl) fullerenes as Potent Free Radical Scavengers, Chemistry Letters, 1998, pp. 465-466.

Da Ros T. et al., Biological Applications of Fullerene Derivatives: A Brief Overview, Croatica Chemica Acta, 2001, pp. 743-755, 74 (4).

Dugan, L. et al., Carboxyfullerenes as neuroprotective agents, Proc. Natl. Acad. Sci USA, Aug. 1997, pp. 9434-9439, vol. 94.

Felder, D. et al., A water soluble methanofullerene derivative: synthesis, micellar aggregation in aqueous solutions, and Incorporation in sol-gel glasses for optical limiting applications, The Royal Society of Chemistry, 2000, pp. 887-892, vol. 10.

Freitas, R.A., Fullerene-Based Pharmaceuticals, Nanomedicine, 2003, 15.3.2.3, vol. IIA: Biocompatibility.

Fuster, M.D. et al, Antioxidative Activities of Heterocyclic Compounds Formed in Brewed Coffee, J. Agit. Food Chem., 2000, pp. 5600-5603, vol. 48, No. 11.

Herranz, M.A. et al., Electroreductive retro-cyclopropanation reactions of nitrophenyl-methanofullerene derivatives, J. Mater. Chem., 2002, abstract only, 12 (7).

Hummelen, J.C. et al., Preparation and Characterization of Fulleroid and Methanofullerene Derivatives, J. Org. Chem., 1995, pp. 532-538, vol. 60, No. 3.

Juha, L. et al., Single-photon photolysis of $C_{60}$, $C_{70}$, $C_{76}$, and $C_{84}$ in solutions, Chemical Physics Letters, 2001, pp. 539-544, 335.

Kamat, P. et al., Radical Reactions of $C_{84}$, Res. Chem. Intermed., 1997, pp. 575-585, vol. 23, No. 7.

Lin, A. et al., Carboxyfullerene Prevents Iron-Induced Oxidative Stress in Rat Brain, Journal of Neurochemistry, 1999, pp. 1634-1640, vol. 72, No. 4.

Rudich, Y. et al., Rate Coefficients for Reactions of $NO_3$ with a Few Olefins and Oxygenated Olefins, J. Phys. Chem., 1996, pp. 5374-5381, vol. 100, No. 13.

Wang, S. et al., Nanomaterials and singlet oxygen photosensitizers: potential applications in photodynamic therapy, The Royal Society of Chemistry, 2004, pp. 487-493, 14.

Wilson, L., Medical Applications of Fullerenes and Metallofullerenes, The Electrochemical Society Interface, Winter 1999, pp. 24-28.

Kronholm, D., Electronic Mail Correspondence entitled "Fullerenes/Nano-C", Dec. 31, 2002.

Kronholm, D. Electronic Mail Correspondence entitled "Konarka Quote", Dec. 19, 2002.

Nano-C, Inc. Advertisement for Commercial-Grade Fullerenes. Chemical and Engineering News, Jul. 21, 2003.

Nano-C, Inc. Advertisement for Industrial Fullerenes. DESIGNFAX, Aug. 2003.

Nano-C, Inc. Archived Nano-C, Inc. website as it existed on Oct. 31, 2003. http://web.archive.org/web/20031031033217/http://www/nano-c/com/derivative.asp.

Dugan, L. et al., "Carboxyfullerenes as neuroprotective agents," Proc. Natl. Acad. Sci. USA, vol. 94, pp. 9434-9439 (Aug. 1997).

Guildi, Dirk M. and Maurizio Prato. "Excited-State Properties of $C_{60}$ Fullerene Derivatives." Acc. Chem. Res. 2000, 33, 695-703.

Arbogast, J.W. et al., Photophysical Properties of C60, J. Phys. Chem. 1991, 95, 11-12.

Arbogast, J.W. et al., Photophysical Properties of C70, J. Am. Chem. Soc. 1991, 113, 8886-8889.

Baumhof, P. et al., A Mild and Effective Method for the Transesterification of Carboxylic Acid Esters, Angew. Chem. Int. Ed., 2001, pp. 3672-3674, vol. 40, No. 19.

Juha, L. et al., Single-photon photolysis of C60, C70, C76, and C84 in solutions, Chem. Phys. Letters 335 (2001) 539-544.

Nishimura, T. et al., A Helical Array of Pendant Fullerenes on an Optically Active Polyphenylacetylene, Angew. Chem. Int. Ed., 2002, pp. 3602-3604, vol. 41, No. 19.

Orfanopoulos, M. et al., Chemical Evidence of Singlet Oxygen Production from C60 and C70 in Aqueous and Other Polar Media, Tetrahedron Letters, vol. 36, No. 3, pp. 435-438, 1995.

Sera, N. et al., Mutagenicity of the fullerene C60-generated singlet oxygen dependent formation of lipid peroxides, Carcinogenesis, vol. 17 No. 10 pp. 2163-2169, 1996.

Wienk, M. et al., Efficient Methano[70]fullerene/MDMO-PPV Bulk Heterojunction Photovoltaic Cells, Angew. Chem., 2003, pp. 3493-3497, vol. 115, Issue 29.

Zheng et al., Methanofullerenes Used as Electron Acceptors in Polymer Photovoltaic Devices, J. Phys. Chem., 2004, pp. 11921-11926, vol. 108.

Guildi, Dirk M. and Maurizio Prato. "Excited-State Properties of $C_{60}$ Fullerene Derivatives." Acc. Chem. Res. 2000, 33, 695-703.

* cited by examiner (a) aqueous HCl/AcOH/1,2-dichlorobenzene; (b) $SOCl_2/CS_2$; (c) ROH/pyridine, where R = C12; (d) ROH/pyridine, where R = $C_8H_{17}O_4$ (e) R-OH/Bu$_2$SnO/1,2-dichlorobenzene/heat; R = C12; C$_8$H$_{17}$O$_4$; or any group.

Experiment setup

HIGHER FULLERENES USEFUL AS RADICAL SCAVENGERS

RELATED APPLICATIONS

This application claims priority under 35 U.S.C. §119(e) to copending U.S. Application Ser. No. 60/529,988, filed on Dec. 15, 2003, entitled "Fullerene Derivatives Useful as Radical Scavengers/Antioxidants," the contents of which are incorporated in their entirety by reference.

This application is related to co-pending application entitled "High Efficiency Fullerene-Based Radical Scavengers," and filed on even date herewith, the contents of which are incorporated in their entirety by reference.

FIELD OF THE INVENTION

This invention relates to fullerene derivatives useful as free radical scavengers.

BACKGROUND

The chemistry of higher fullerenes has been explored little due to the historical low availability and high price. As used herein, "higher fullerenes" refer to fullerenes containing more than 70 carbon atoms. $C_{60}$ and $C_{70}$ have been shown to be excellent radical scavengers, but the radical scavenging abilities of fullerenes such as $C_{84}$, and other fullerenes higher in molecular weight than $C_{70}$ are little known or totally unknown. The relative radical scavenging efficiencies of different fullerenes may be altered due to different number of graphitic bonds, difference in energy strain (correlated to the degree of flatness which typically increases with increasing fullerene molecular weight), the electron affinities, HOMO-LUMO gaps, etc., any or all of which could contribute to relative differences in the efficiency of different fullerenes to scavenge radicals, and affect the resulting utility of different fullerenes in different applications. Chiang (Chemistry Letters 1998) has shown that different $C_{60}$ fullerene derivatives which have different strains and/or electron affinities show significantly different radical scavenging efficiencies, and that this relative difference is not predictable a priori from the structure of the derivatives and resulting alterations to the $C_{60}$ cage. Similarly, differences relative to the $C_{60}$ cage resulting from changes in the number of carbons and changes to the bond nature and electronic structure of higher fullerenes relative to $C_{60}$ may give significant differences in radical scavenging efficiency. Therefore, the radical scavenging efficiencies and utility of different higher fullerenes are difficult to predict from physical or chemical theories or considerations.

Current commercial-type production methods such as combustion produce sufficient quantities of such fullerenes to make them interesting for a variety of applications, including but not limited to pharmaceuticals and personal care, where radical scavenging, or antioxidant, capacity can be very beneficial.

Because of the high quantum yield of triplet states, $C_{60}$ is known to be an efficient producer of singlet $O_2$, a reactive oxygen species (ROS) under irradiation. ROS are known to be detrimental to human health and lead to lipid peroxidation, neural damage, skin damage, and other destructive biochemical processes. Use of $C_{60}$ as, for example, an antioxidant for prevention of skin damage may also lead to production of singlet $O_2$ in the presence of sunlight or other irradiation, which in turn may damage the skin. Similarly, the generation of singlet $O_2$ may be undesirable for other reasons, such as in chemical reactions where radical scavenging is desired without the generation of singlet $O_2$, which could react in undesired side reactions. Further, the formation of triplet states of $C_{60}$ and $C_{70}$ results in differences in reduction potential (electron accepting ability), so that in redox reaction systems where electron accepting ability of the fullerene leads to undesired chemical pathways, it would be beneficial to have a fullerene that had lower quantum yields of the triplet states. Further still, the triplet states of $C_{60}$ and $C_{70}$ may result in energy transfer processes leading to other singlet or triplet states of molecules other than oxygen, resulting in undesired alterations in reactivity of these molecules. Preserving the radical scavenging benefits demonstrated for the fullerenes $C_{60}$ and $C_{70}$, namely their high efficiencies of radical scavenging, while minimizing or preventing effects resulting from the high quantum yield of triplet states of $C_{60}$ and $C_{70}$, including but not limited to the production of singlet $O_2$, would be highly beneficial.

SUMMARY

It has been surprisingly discovered that $C_{84}$ is at least as efficient in scavenging free radicals as $C_{60}$. Also, under certain conditions it has been observed that $C_{60}$ may exhibit an increase in radical formation, or pro-oxidant activity, and under the same conditions, it has been observed that $C_{84}$ does not exhibit pro-oxidant activity, and further, exhibits what may be antioxidant activity. Compositions for and methods of reducing the levels of free radicals in a target are disclosed. Compositions for and methods of reducing the levels of free radicals without generation of fullerene triplet excited states, which may lead to singlet oxygen, or other undesired consequences in a target are disclosed.

In one aspect of the present invention, higher fullerenes suitable for use as free radical scavengers are disclosed. Higher fullerenes, in particular $C_{84}$, maintain the radical scavenging benefits of the all-carbon closed cage structure of fullerenes, are amenable to chemical derivatization for alteration of physical properties such as solubility, and cause less undesired consequences, such as pro-oxidant activity, which may be a result of fullerene triplet states such as production of singlet $O_2$ under irradiation. Higher fullerenes and higher fullerene derivatives are thus very useful in applications where radical scavenging is desirable, but the formation of pro-oxidant activity resulting from fullerene triplet states and/or consequences such as singlet $O_2$ production, or other effects, are undesired.

In one aspect of the invention, a method is provided for the scavenging (or reduction) of free radicals from a target. The target is exposed to a class of higher fullerene derivatives to reduce the level of free radicals in the target, without sufficient increase in the undesired consequences such as pro-oxidant activity resulting from fullerene triplet states and/or resulting generation of singlet oxygen, or other effects are undesired. The class of compounds useful as free radical scavengers may be functionalized with chemical moieties so that the chemical and/or physical properties of the fullerene may be altered without significant alteration of the inherent physical and chemical nature of the fullerene cage so as to preserve the radical scavenging efficiency of the fullerene cage.

In one aspect, a method of scavenging free radicals in or around a target includes exposing a target to a free radical scavenging compound selected from the group consisting of $C_{84}$ and derivatives thereof in an amount and for a time sufficient to reduce the levels of free radicals in or around the target.

In one or more embodiments, the free radical scavenger compound does not significantly increase pro-oxidant activity due to triplet excited states of the free radical scavenger compound.

In one or more embodiments, the target is a dermal or mucosal substrate.

In one or more embodiments, the free radical scavenging compound has the general formula, $C_{84}(Y)_m$, $C_{84}$ is a fullerene, and where Y is a moiety attached, directly or indirectly, to the fullerene, where m is in the range of 1 to about 30, and wherein Y is selected from the group consisting of lipophilic moieties, hydrophilic moieties, amphiphilic moieties, free radical scavenging moieties, or bio-site specific moieties.

In one or more embodiments, Y includes a lipophilic moiety and the lipophilic moiety is selected from the group consisting of alkanes, fatty acid, fatty esteramine, fatty alcohols, and fatty amine moieties, and the compound is capable of transport through or solubilization in lipid phases in a biological system.

In one or more embodiments, Y includes a hydrophilic moiety, and the hydrophilic moiety is selected from the group consisting of poly-(ethylene oxide)s, mono-, di- or poly-hydroxylated alkanes, mono-, di- or poly-hydroxylated cycloalkanes, amino alkanes, diamino alkanes, mono-, di-, or polysaccharides, hydroxides, ammonium groups, alkylated ammonium groups, phosphates, alkylphosphates, sulfonates, and alkylsulfonates, phosphonium groups, carboxylate groups, sulfonic acid groups, iminium groups, imidine groups, and imidinium groups. The compound is capable of transport through or solubilization in aqueous phases in a biological system.

In one or more embodiments, Y includes a chemical moiety that is independently effective as a free radical scavenger.

In one or more embodiments, Y includes an amphiphilic moiety, and the amphiphilic moiety is selected from the group consisting of polyethylene glycol, poly(ethylene oxide)s, propylene glycol, poly(propylene glycol), hexylene glycol, diethylene glycol, propylene glycol n-alkanols, and glycol moieties.

In one or more embodiments, Y includes a moiety which addresses a biological target such as [monoclonal] antibodies, proteins, enzymes, protein hormones, membrane proteins, steroids, coenzymes, co-factors, [oligo] DNA, RNA, enzyme inhibitors, enzyme substrates, specific cells or organs, tissues.

In another aspect, a method of scavenging free radicals in or around a target includes exposing a target to a compound having the formula,

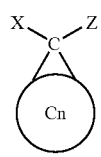

where the ring, Cn, is fullerene $C_{84}$; where X and Z are the same or different, and where X or Z are independently selected from the group consisting of lipophilic moieties, hydrophilic moieties, amphiphilic moieties, free radical scavenging moieties, in an amount and for a time sufficient to reduce the levels of free radicals in or around the target.

In one or more embodiments, the free radical scavenger compound does not significantly increase pro-oxidant activity due to triplet excited states of the free radical scavenger compound;

In one or more embodiments, the lipophilic moiety is selected from the group consisting of alkanes, fatty acid, fatty esteramine, fatty alcohol, and fatty amine moieties, and the compound is capable of transport through or solubilization in lipid phases in a biological system.

In one or more embodiments, X or Z includes a hydrophilic moiety, and the hydrophilic moiety is selected from the group consisting of poly-(ethylene oxide)s, mono-, di- or poly-hydroxylated alkanes, mono-, di- or poly-hydroxylated cycloalkanes, amino alkanes, diamino alkanes, mono-, di-, or polysaccharides, hydroxides, ammonium groups, alkylated ammonium groups, phosphates, alkylphosphates, sulfonates, and alkylsulfonates, phosphonium groups, carboxylate groups, sulfonic acid groups, iminium groups, imidine groups, and imidinium groups.

In one or more embodiments, one or more of X and Z includes a chemical moiety that is independently effective as a free radical scavenger or a non-electron withdrawing group.

In one or more embodiments, one or more of X and Z includes an amphiphilic moiety, and the amphiphilic compound is selected from the group consisting of polyethylene glycol, poly(ethylene oxide)s, propylene glycol, poly(propylene glycol), hexylene glycol, diethylene glycol, propylene glycol n-alkanols, and glycol moieties.

In one or more embodiments, the non-electron withdrawing group is selected from the group consisting of alkyls, cyclic alkyls, substituted alkyls, alkylaryls, alkyl ethers, alkylaryl ethers, alkyl thioethers, alkylaryl thioethers, alkyl esters, alkylaryl esters, alkyl thioesters, alkylaryl thioesters, alkyl amides, alkylaryl amides, alkyl amines, alkylaryl amines, alkyl anhydrides, alkylaryl anhydrides, alkyl carbonates (or carboxylic acids), alkylaryl carbonates, arylalkyls, aryl ethers, arylalkyl ethers, aryl thioethers, arylalkyl thioethers, aryl esters, arylalkyl esters, aryl thioesters, arylalkyl thioesters, aryl amides, arylalkyl amides, aryl amines, arylalkyl amines, aryl anhydrides, arylalkyl anhydrides, aryl carbonates (or carboxylic acids) and arylalkyl carbonates.

The method may further include exposing the target to at least one additional radical scavenging compound, or an additive selected to enhance or preserve the efficacy of the compound.

In another aspect, a free radical scavenging compound is provided having the formula,

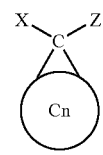

where the ring, Cn, is fullerene $C_{84}$, where X is $(C')(R')_n$ and C' is an aryl carbon and X is selected from the group consisting of aryl, substituted aryl, heteroaryl, substituted heteroaryl moieties; R' is independently selected such that X is a non-electron withdrawing group, and n=2; and Z is $(C'')(R'')_n$ and C'' is a carbon atom selected from the group consisting of alkyl, alkenyl, alkynyl, and aromatic carbons and R'' is independently selected such that Z is a non-electron withdrawing group, and n=1, 2, or 3.

In one or more embodiments, X=X' and Z=(A)(C'=Q')(Z')(Y'), where X' is selected from the group consisting of aryl group, substituted aryl group, a heteroaryl and a substituted heteroaryl; A is an aliphatic group containing 1 to 20 carbon atoms; Q' is O, N or S; Z' is halogen, O, N, or S; and Z' is bound to C'; and Y' is any chemical group bound to Z'; and any salts thereof.

In one or more embodiments, C' is an aryl carbon and X is selected from the group consisting of aryl, substituted aryl, heteroaryl, substituted heteroaryl moieties and Z is $(C'')(R'')_n$ and C'' is a carbon atom selected from the group consisting of alkyl, alkenyl, alkynyl, and aromatic carbons and R'' is independently selected such that Z is a non-electron withdrawing group.

In one or more embodiments, C' is an aryl carbon and X is selected from the group consisting of aryl, substituted aryl, heteroaryl, substituted heteroaryl moieties and Z is $(C'')(R'')_n$ and C'' is an alkyl carbon and Z is independently selected from the group consisting of alkyl moieties and alkyl moieties bearing a hetero or functional group.

In one or more embodiments,

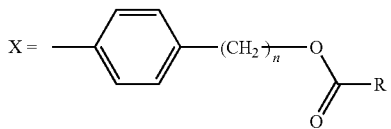

where n is in the range of 1 to 20, and R is any chemical group.

In one or more embodiments, R is selected from the group consisting of aryl, substituted aryl, heteroaryl, substituted heteroaryl moieties, the group consisting of alkyl moieties and alkyl moieties bearing a hetero or functional group.

In one or more embodiments, the compound contains two to four C(X)(Z) adducts on the fullerene ring, and the fullerene compound is a [5,6] fulleroid or a [6,6] methanofullerene.

In one or more embodiments, the non-electron withdrawing group is selected from the group consisting of alkyls, cyclic alkyls, substituted alkyls, alkylaryls, alkyl ethers, alkylaryl ethers, alkyl thioethers, alkylaryl thioethers, alkyl esters, alkylaryl esters, alkyl thioesters, alkylaryl thioesters, alkyl amides, alkylaryl amides, alkyl amines, alkylaryl amines, alkyl anhydrides, alkylaryl anhydrides, alkyl carbonates (or carboxylic acids), alkylaryl carbonates, arylalkyls, aryl ethers, arylalkyl ethers, aryl thioethers, arylalkyl thioethers, aryl esters, arylalkyl esters, aryl thioesters, arylalkyl thioesters, aryl amides, arylalkyl amides, aryl amines, arylalkyl amines, aryl anhydrides, arylalkyl anhydrides, aryl carbonates (or carboxylic acids)X and arylalkyl carbonates. Z are different.

In one or more embodiments, the compound is capable of reducing levels of free radicals in or around a target without significantly increasing pro-oxidant activity, such as by avoidance of triplet excited states of the free radical scavenger compound.

In one or more embodiments, one or more of X and Y includes a lipophilic moiety, and the lipophilic moiety is selected from the group consisting fatty acid, fatty amine, fatty alcohol, and fatty amine moieties.

In one or more embodiments, one or more of X and Y includes a hydrophilic moiety, or
a chemical moiety that is independently effective as a free radical scavenger.

In one or more embodiments, one or more of X and Y comprises an amphiphilic moiety, and the amphiphilic compound is selected from the group consisting of polyethylene glycol, poly(ethylene oxide)s, propylene glycol, hexylene glycol, diethylene glycol, propylene glycol n-alkanols, and glycol moieties.

In one or more embodiments, one or more of X and Y is a non-electron withdrawing group, and the non-electron withdrawing group is selected from the group consisting of alkyls, cyclic alkyls, substituted alkyls, alkylaryls, alkyl ethers, alkylaryl ethers, alkyl thioethers, alkylaryl thioethers, alkyl esters, alkylaryl esters, alkyl thioesters, alkylaryl thioesters, alkyl amides, alkylaryl amides, alkyl amines, alkylaryl amines, alkyl anhydrides, alkylaryl anhydrides, alkyl carbonates (or carboxylic acids), alkylaryl carbonates, arylalkyls, aryl ethers, arylalkyl ethers, aryl thioethers, arylalkyl thioethers, aryl esters, arylalkyl esters, aryl thioesters, arylalkyl thioesters, aryl amides, arylalkyl amides, aryl amines, arylalkyl amines, aryl anhydrides, arylalkyl anhydrides, aryl carbonates (or carboxylic acids) and arylalkyl carbonates.

In yet another aspect, a method of altering radical mediated chemical pathways in a biological system includes reacting a radical species present in a biological system with a compound selected from the group consisting of $C_{84}$ and functionalized derivatives thereof in an amount and for a time sufficient to reduce the levels of free radicals in or around the target.

In yet another aspect, a method of reducing oxidative stress in a biological system includes reacting a radical species present in a biological system with a compound selected from the group consisting of $C_{84}$ and functionalized derivatives thereof in an amount and for a time sufficient to reduce the levels of free radicals in or around the target.

In yet another aspect, a method of preventing or reducing lipid peroxidation in a biological system includes exposing a biological system to a compound selected from the group consisting of $C_{84}$ and functionalized derivatives thereof in an amount and for a time sufficient to reduce the levels of free radicals in or around the target.

In one or more embodiments, the free radical scavenger compound does not significantly increase pro-oxidant activity due to triplet excited states of the free radical scavenger compound;

In one or more embodiments, the free radical scavenging compound has the general formula, $C_n(Y)_m$, where $C_x$ is $C_{84}$ fullerene, and where Y is a moiety attached, directly or indirectly, to the fullerene, where m is in the range of 1 to 30, and wherein Y is selected from the group consisting of lipophilic moieties, hydrophilic moieties, amphiphilic moieties, free radical scavenging moieties.

A composition also is provided including a biologically compatible carrier; and a compound having the formula,

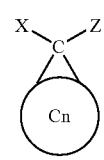

1 where the ring, $C_n$ is a fullerene $C_{84}$; where X and Z are the same or different, and where X or Z are independently selected from the group consisting of lipophilic moieties, hydrophilic moieties, amphiphilic moieties, free radical scavenging moieties, in an amount and for a time sufficient to reduce the levels of free radicals in or around the target without significantly increasing pro-oxidant activity due to triplet excited states of the free radical scavenger compound.

BRIEF DESCRIPTION OF THE DRAWING

Various embodiments of the invention are described with reference to the figures, which are provided for the purpose of illustration only and are not intended to be limiting of the invention, the full scope of which is set forth in the claims below.

DETAILED DESCRIPTION

Figure 1:
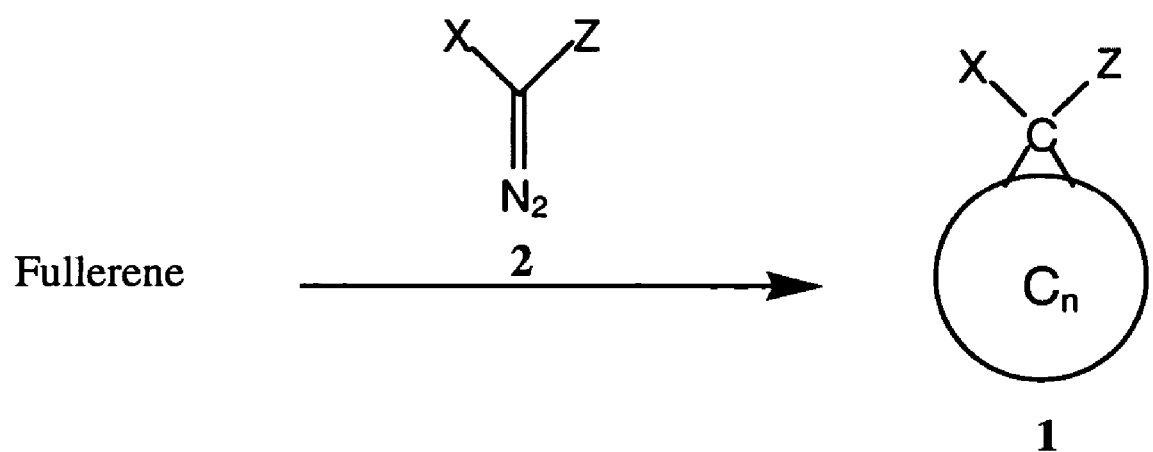
FIG. 1 is general scheme for the preparation of a substituted higher methanofullerene by reaction with a diazo compound.

While $C_{60}$ and $C_{70}$ are known to be highly efficient free radical scavengers they are also known to have a high quantum yield of the triplet state (e.g., by photoactivation) which results in efficient generation of other energetic species such as singlet oxygen. In many cases, free radical scavenging by $C_{60}$ and $C_{70}$ is desirably conducted in the absence of light (photons) where generation of $C_{60}$ and $C_{70}$ triplet states and resulting singlet oxygen is to be avoided. The damaging effect of singlet oxygen on biological systems is well known. In topical or dermal applications for pharmaceutical or cosmeceutical purposes where singlet oxygen generation is problematic, alternative fullerene free radical scavengers are desired.

$C_{76}$ and $C_{84}$ are significantly more photostable than $C_{60}$ and $C_{70}$. Juha et al. report the following quantum yields of fullerene photolysis ($\phi_p$) and singlet oxygen production ($\phi_\Delta$) for $C_{60}$, $C_{70}$, $C_{76}$ and $C_{84}$. Thus, $C_{76}$ and $C_{84}$ produce only a small fraction of the singlet oxygen produced by $C_{60}$ and $C_{70}$ under comparable conditions, due to the low quantum yield of triplet states generated by photoactivation.

TABLE 1

Estimated relative quantum yields of fullerene photolysis ($\phi_p$) induced by $Ar^+$ laser ($\lambda = 476.5$ nm) and singlet oxygen production ($\phi_\Delta$) photosensitized by fullerenes in tetrachloroethylene and toluene

| Fullerene | Tetrachloroethylene | | Toluene $\phi_\Delta^b$ |
| | $\phi_p^a$ | $\phi_\Delta^b$ | |
|---|---|---|---|
| $C_{60}$ | $1.00^c$ | —$^d$ | —$^d$ |
| $C_{70}$ | 0.2 | $1.00^e$ | $1.00^e$ |
| $C_{76}$ | 0.03 | 0.15 | 0.12 |
| $C_{84}$ | 0.002 | 0.11 | 0.06 |

$^a$Experimental error ±20%.
$^b$Experimental error ±15%.
$^c$Arbitrarily chosen value.
$^d$Note that according to [21-26, 35] we can consider $\phi_\Delta$ ($C_{60}$) ≈ $\phi_\Delta$ ($C_{70}$).
$^e$Arbitrary value which is close to the experimental values of $\phi_\Delta$ ($C_{70}$) in benzene [22, 24, 26, 35].
Juha et al., Chem. Phys. Lett. 335 (2001) 539-544.

Although the various fullerenes differ significantly in the possible energetic states resulting from photoactivation, resulting generation of triplet states, and resulting propensity to produce singlet oxygen, it has been surprisingly discovered that $C_{84}$ is highly effective free radical scavengers, and may be at least as efficient a free radical scavenger as $C_{60}$. Further it has been surprisingly discovered that under certain conditions in complex reaction systems of practical interest, even without significant irradiation, and in which $C_{60}$ acts as a pro-oxidant, $C_{84}$ has the highly beneficial aspect of not acting as a pro-oxidant. Tests directed to the determination of the free radical scavenging effectiveness of $C_{84}$ and [6,6]-phenyl C61-butyric acid methyl ester ([60]PCBM), a $C_{60}$ derivative, to free radicals present in cigarette smoke (predominantly peroxy radicals) established that $C_{84}$ is as effective a free radical scavenger as [60]PCBM or a better free radical scavenger than [60]PCBM. See FIG. 6A, below.

Further, in similar tests comparing $C_{84}$ to $C_{60}$ in decalin containing tetralin as an impurity, which may act as an H-donor radical scavenger, and with more efficient mass transport of the smoke into the solvent, $C_{60}$ is observed to act apparently as a pro-oxidant even in the absence of direct light, while $C_{84}$ does not exhibit what could be pro-oxidant activity, and even shows apparently antioxidant activity. This system is highly complex, with multiple radical and non-radical species in the smoke, and an H-donor radical scavenger present in high concentration (tetralin) relative to the fullerene concentrations in the solvent. It is possible that the radical reaction network is altered differently by $C_{60}$ and $C_{84}$ due to the differing triplet states and energy transfer in processes not photoactivated, or that even small amounts of photoactivation result in significant effects.

The high free radical scavenging efficiency of $C_{84}$, coupled with their low yield of triplet excited states, and/or their resulting low singlet oxygen production, makes these compounds and their functionalized derivatives excellent candidates for free radical scavenging applications where generation of fullerene triplet states and/or singlet oxygen generation during use is desirably avoided.

In one aspect, higher fullerenes, e.g., $C_{84}$ and derivatives of these higher fullerenes, as well as fullerene mixtures comprising higher fullerenes and/or higher fullerene chemical derivatives, are used as radical scavengers for applications where radical scavenging is a desired property, and minimization of other undesirable effects such as pro-oxidant behavior, which may be the result of triplet state generation, singlet $O_2$ production, or other properties of higher fullerenes, is beneficial.

In one or more embodiments, a method is provide for reducing the level of free radicals in a system while avoiding or reducing the undesired side-effects of $C_{60}$ and $C_{70}$, such as pro-oxidant activity, and/or high yield of triplet states, and/or level of singlet oxygen production. The method includes exposing a target to a compound selected from the group consisting of $C_{84}$ and chemically functionalized derivatives thereof in an amount and for a time sufficient to reduce the levels of free radicals in the target without producing undesired side effects such as pro-oxidant activity, and/or high yield of triplet states, and/or level of singlet oxygen production on the target.

The target can be a biological system, e.g., microorganisms, plants, animals, humans, and cells, tissues, and organs thereon, that is sensitive to or detrimentally affected by undesirable features of $C_{60}$ and $C_{70}$, such as pro-oxidant activity, and/or high yield of triplet states, and/or level of singlet oxygen production. For example, the target can be a dermal membrane, mucosal membrane, micro-biological target such as DNA, biological target such as a lipid membrane, or other membrane surface or organ. The method may be used for dermatological and cosmeceutical applications, where exposure to light typically cannot be practically avoided. Non-physiological uses are also envisioned herein, such as use as polymer stabilizers, in which case the target is the polymer composition.

The compound can be delivered to the target in a carrier vehicle. The free radical scavenging compounds may be administered to the target in solution, or in suspension. They may be prepared as a pharmaceutical composition using conventional forms for oral, topical, intramuscular, subcutaneous, and intravenous administration. Suitable carrier vehicles include those typically employed in the dermal, application of pharmaceutical and cosmetic materials.

The effective dose of the higher fullerene free radical scavenging compound depends upon the manner of administration and condition of the biological system or patient to be treated. Methods of administration involve the step of bringing the higher fullerene free radical scavenging compound in a suitable carrier into contact with a target or a biological system or patient for treatment.

For application of fullerenes as radical scavengers in various settings, it is useful to employ fullerene derivatives which preserve the high efficiency of the radical scavenging properties of the fullerene cage to the highest extent possible without detrimentally altering the electron affinity, energetic strain, number of reactive sites, steric availability, etc. of the fullerene cage. Further, it is useful to form fullerene derivative intermediates to allow for formation of a variety of new fullerene derivatives with various functionalities, e.g., lipophilic, hydrophilic or amphiphilic fullerenes, that do not significantly differ in radical scavenging efficiency from their fullerene parent.

In one or more embodiments, the compound for use in the methods described herein have the general formula $C_n(Y)_m$, where $C_n$ is $C_{84}$, and where Y is a moiety attached, directly or indirectly, to the fullerene cage and m is in the range of 1 to about 30, preferably in the range of 1 to about 20. Y can possess lipophilic (or hydrophobic), hydrophilic or amphiphilic properties. It can include chemical moieties that provide biofunctionality or that are independently free radical scavengers. It can also be a polymer, in which case the $C_n$ moiety is tethered to the polymer.

In one or more embodiments, Y includes chemical moieties that provide lipophilic (or hydrophobic) functionality, i.e., having an affinity for lipid-like materials. Lipids include fat-like substances characterized by being water insoluble and being extractable by nonpolar (or fat) solvents such as alcohol, ether, chloroform, benzene, etc. All contain as a major constituent aliphatic hydrocarbons. Suitable lipophilic moieties for use in free radical scavenging include long-chain alkanes or substituted long-chain alkanes (6 or more carbon atoms, or 10 carbon atoms or 12 carbon atoms or 16 or more carbon atoms), which may be branched, and which may contain various other chemical groups that have affinity with lipids. Compounds containing lipophilic moieties are useful in the transport of the free radical scavenging compound through lipid phases in a biological system or hydrophobic phases in a chemical system.

Exemplary lipophilic groups include fatty alcohol and fatty acid ester, fatty amide, fatty amine moieties, such as isostearic acid derivatives, or functional groups derived from molecules such as isopropyl palmitate, isopropyl isostearate, stearyl stearate, diisopropyl adipate, octyl palmitate, isopropyl palmitate, cetyl lactate, cetyl ricinoleate, tocopheryl acetate, acetylated lanolin alcohol, cetyl acetate, glyceryl oleate, methyl oleate, isobutyl oleate, tocopheryl linoleate, arachidyl propionate, myristyl lactate, decyl oleate, isopropyl lanolate, neopentylglycol dicaprylate/dicaprate, isononyl isononanoate, isotridecyl isononanoate, myristyl myristate, octyl dodecanol, sucrose esters of fatty acids, octyl hydroxystearate, stearamide, oleamide, and erucamide, and the like.

In one or more embodiments, Y includes chemical moieties that provide hydrophilic functionality, i.e., having an affinity to water or hydrophilic materials. Groups which may provide hydrophilic functionality include poly-(ethylene oxide)s, mono-, di- or poly-hydroxylated alkanes, mono-, di- or poly-hydroxylated cycloalkanes, amino alkanes, diamino alkanes, mono-, di-, or poly-saccharides, hydroxides, ammonium groups, alkylated ammonium groups, phosphates, alkylphosphates, sulfonates, alkylsulfonates, phosphonium groups, carboxylate groups, sulfonic acid groups, iminium groups, imidine groups, and imidinium groups. Compounds containing hydrophilic moieties are useful in the transport of the free radical scavenging compound through aqueous phases in a biological or chemical system. One or more hydrophilic Y-groups can be linked to a carbon of the higher fullerene. For example, the higher fullerene is functionalized with one to about 30 hydroxyl groups, or one to about 10 hexasulfobutyl groups, sulfonate groups or alkyl sulfonate groups to render the compound water soluble.

In one or more embodiments, Y includes chemical moieties that provide amphiphilic functionality. Amphiphilic functionality refers to molecules which have both lipophilicity and hydrophilicity. Groups which provide amphiphilic functionality include polyethylene glycol, poly(ethylene oxide)s, propylene glycol, hexylene glycol, diethylene glycol, propylene glycol n-alkanols, and other glycol moieties. Alternatively, amphiphilic properties may be obtained by selecting lipophilic and hydrophilic properties for multiple Y-substituents.

In still other embodiments, Y includes chemical moieties that provide biofunctionality. Biofunctionality is useful to improve the solubility, miscibility, or transport of the higher fullerenes in a biological system. It may be useful to identify and bind to the appropriate biological target. Thus, Y may be a sugar, histamine, amino acid or carotenoid and the like. The Y group may also include a chemical moiety that is independently effective as a free radical, for example, phenolics, polyphenolics, flavenoids, carotenoids, anthocyanidins, lipoic acids, ubiquinoids, retinoids or Vitamin E moieties and the like. In still other embodiments, Y includes chemical moieties that provide biofunctionality for specific targeting of biological targets. Thus Y may be [monoclonal] antibodies, other proteins, {e.g., enzymes, protein hormones, membrane proteins, etc.}, steroids, coenzymes, co-factors, [oligo] DNA, RNA, enzyme inhibitors, enzyme substrates, specific cells or organs, tissues, and so on.

Various methanofullerenes of higher fullerenes can be used as radical scavengers having low singlet oxygen production. "Methanofullerenes" refer to methano-bridged fullerenes that form a cyclopropyl ring adduct with the fullerene cage. The methylene carbon of the cyclopropyl ring is referred to as the "methanocarbon." The chemical and/or physical functionality of the fullerene is adjusted by modification of pendant groups at the methanocarbon instead of the fullerene cage. Modifications are provided to obtain enhanced lipophilicity, hydrophilicity, amphiphilicity or other properties of the methanofullerene. In one or more embodiments, at least one of the methanocarbon pendant groups is a non-electron withdrawing, or even an electron donating group. The absence or reduction of electron withdrawal on the fullerene cage helps to maintain the free radical scavenging capability of the fullerene molecule.

A free radical may be scavenged from on or in a target by exposing the target to a compound having the formula,

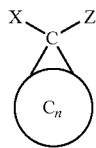

1 where the ring, $C_n$, is $C_{84}$, where X and Z are the same or different, and where X or Z are independently selected from the group consisting of lipophilic moieties, hydrophilic moieties, amphiphilic moieties, free radical scavenging moieties.

In one or more embodiments, X and/or Z includes chemical moieties that provide lipophilic (or hydrophobic) functionality, i.e., having an affinity for lipid-like materials. Lipids include fatlike substances characterized by being water insoluble and being extractable by nonpolar (or fat) solvents such as alcohol, ether, chloroform, benzene, etc. All contain as a major constituent aliphatic hydrocarbons. Suitable lipophilic moieties for use in free radical scavenging include long-chain alkanes or substituted long-chain alkanes (6 or more carbon atoms, or 10 carbon atoms or 12 carbon atoms or 16 or more carbon atoms), which may be branched, and which may contain various other chemical groups having affinity with lipids. Compounds containing lipophilic moieties are useful in the transport of the free radical scavenging compound through lipid phases in a biological system or hydrophobic phases in a chemical system.

Exemplary lipophilic groups include fatty alcohol and fatty acid ester, fatty amide, fatty amine moieties, such as isostearic acid derivatives, or functional groups derived from molecules such as isopropyl palmitate, isopropyl isostearate, stearyl stearate, diisopropyl adipate, octyl palmitate, isopropyl palmitate, cetyl lactate, cetyl ricinoleate, tocopheryl acetate, acetylated lanolin alcohol, cetyl acetate, glyceryl oleate, methyl oleate, isobutyl oleate, tocopheryl linoleate, arachidyl propionate, myristyl lactate, decyl oleate, isopropyl lanolate, neopentylglycol dicaprylate/dicaprate, isononyl isononanoate, isotridecyl isononanoate, myristyl myristate, octyl dodecanol, sucrose esters of fatty acids, octyl hydroxystearate, stearamide, oleamide, and erucamide In one or more embodiments, X and/or Z includes chemical moieties that provide hydrophilic functionality, i.e., having an affinity to water or hydrophilic materials. Groups which may provide hydrophilic functionality include poly-(ethylene oxide)s, mono-, di- or poly-hydroxylated alkanes, mono-, di- or poly-hydroxylated cycloalkanes, amino alkanes, diamino alkanes, mono-, di-, or poly-saccharides, hydroxides, ammonium groups, alkylated ammonium groups, phosphates, alkyl phosphates, sulfonates, and alkyl sulfonates, phosphonium groups, carboxylate groups, sulfonic acid groups, iminium groups, imidine groups, and imidinium groups. Compounds containing hydrophilic moieties are useful in the transport of the free radical scavenging compound through aqueous phases in a biological or chemical system. One or more hydrophilic X- and/or Z-groups can be linked to a methanocarbon of the higher fullerene. For example, the higher fullerene is functionalized with one to about 30 hydroxyl groups, or one to about 10 hexasulfobutyl groups, sulfonate groups or alkyl sulfonate groups to render the compound water soluble.

In one or more embodiments, X and/or Z includes chemical moieties that provide amphiphilic functionality. Amphiphilic functionality refers to molecules which have both lipophilicity and hydrophilicity. Groups which provide amphiphilic functionality include polyethylene glycol, poly(ethylene oxide)s, propylene glycol, hexylene glycol, diethylene glycol, propylene glycol n-alkanols, and other glycol moieties. Alternatively, amphiphilic properties may be obtained by selecting lipophilic and hydrophilic properties for multiple X- or Z-substituents.

In still other embodiments, X and/or Z includes chemical moieties that provide biofunctionality. Biofunctionality is useful to improve solubility, miscibility, or transport of the higher fullerenes in a biological system. It may be useful to identify and bind to the appropriate biological target. Thus, X and/or Z may be a sugar, histamine, amino acid or carotenoid and the like. The X and/or Z group may also include a chemical moiety that is independently effective as a free radical, for example, flavenoids, carotenoids, anthocyanidins, lipoic acids, ubiquinoids, retinoids or Vitamin E moieties and the like.

In still other embodiments, X and/or Z includes chemical moieties that provide biofunctionality for specific targeting of biological targets. Thus Y may be [monoclonal] antibodies, other proteins, {e.g., enzymes, protein hormones, membrane proteins, etc.}, steroids, coenzymes, co-factors, [oligo] DNA, RNA, enzyme inhibitors, enzyme substrates, specific cells or organs, tissues, and so on.

In one or more embodiments, X and/or Z is a non-electron withdrawing group or an electron donating group. By way of example, the groups may include alkyls, cyclic alkyls, and substituted alkyls, alkylaryls, alkyl ethers, alkylaryl ethers, alkyl thioethers, alkylaryl thioethers, alkyl esters, alkylaryl esters, alkyl thioesters, alkylaryl thioesters, alkyl amides, alkylaryl amides, alkyl amines, alkylaryl amines, alkyl anhydrides, alkylaryl anhydrides, alkyl carbonates (or carboxylic acids) and alkylaryl carbonates. By way of example, the groups may include substituted aryls such as arylalkyls, aryl ethers, arylalkyl ethers, aryl thioethers, arylalkyl thioethers, aryl esters, arylalkyl esters, aryl thioesters, arylalkyl thioesters, aryl amides, arylalkyl amides, aryl amines, arylalkyl amines, aryl anhydrides, arylalkyl anhydrides, aryl carbonates (or carboxylic acids) and arylalkyl carbonates. Other substitutes are contemplated within the scope of the invention.

Other exemplary non-electron withdrawing groups are obtained by including an alpha-carbon lacking a double or triple bond to an electronegative atom such as O, N or S in one or more of the functional groups pendant to the methanocarbon. Aromatic, alkyl, alkenyl, and alkynyl alpha-carbons are linked to an additional chemical moiety or H. By directly linking electron donating or electron neutral moieties at the methanocarbon, the electronic and chemical integrity of the fullerene cage is better preserved. Electron withdrawing groups or other moieties may be tethered to the fullerene at a distance from the fullerene, without these groups being in close proximity to the fullerene cage, so as to preserve the inherent radical scavenging efficiency of the fullerene. Such electron withdrawing functional groups may be desirable to accomplish other objectives of the molecule, such as, attaining desired solubility, transport or binding characteristics.

It is contemplated that a Y group may be linked directly to the fullerene cage. Y may be a group as described herein above. Y may be linked to the fullerene via a methano-bridge or other functional bond.

The free radical scavenging higher fullerene compounds may have one or more methanofullerene adducts. By "adduct" as the term is used with reference to methanofullerenes, it is meant the addition of a methylene group to the fullerene cage resulting in the formation of a cyclopropane ring. Functional groups may be attached to the available sites on the methanocarbon.

Methanofullerenes having a minimal number of adducts, e.g., a monoadduct or 2-3 adducts, allows the alteration of the chemical and physical properties of the fullerene in a desirable way, while preserving to a great degree the strain and number of olefin bonds, steric availability, and other properties of the fullerene cage. The absence or reduction of electron-withdrawing groups adjacent to the fullerene cage also maintain or enhance free radical scavenging efficiencies.

In particular, monoadducts provide for the least disruption of the chemical and physical nature of the fullerene cage, and allow for convenient synthesis of single isomers. However, di, tri and higher adducts may be used in the radical scavenging processes described herein.

Further still, it is useful to have a common addition chemistry through which chemical moieties having various functionalities may be added to a fullerene.

Various methanofullerenes are known in the art, and synthesis of these compounds through diazoalkane addition chemistry has the advantage of being simple synthetic chemistry and providing monoadducts in high yield. This reaction is illustrated schematically in FIG. 1. A fullerene compound may be reacted with a diazo compound 2 to provide the functionalized methanofullerene 1. Diazoalkane addition results first in [6,6] diazoline adducts that can expel $N_2$ and yield [5,6] fulleroids, which can be isomerized to [6,6] methano-bridged fullerenes, otherwise known as cyclopropa fullerenes (referred to herein as methanofullerenes). The carbon atom in the cyclopropa fullerene is termed the methanocarbon. X and Z of the diazo compound 2 can be moieties as described herein for the methanofullerene compound or they may be intermediates containing reactive groups capable of further reaction to form the desired X, Z functional groups of the methanocarbon. Further, similar diazoalkane addition chemistry may be used to form multiple fullerene derivatives using different diazoalkane precursors, which can be synthesized conveniently in a large variety. This provides a synthetic route to variously substituted methanofullerene compounds that may be used in the free radical scavenging processes described herein.

The fullerene derivative [6,6]-phenyl $C_{61}$-butyric acid methyl ester (PCBM) 3 is an example of a fullerene derivative formed through diazoalkane addition chemistry, where the diazoalkane is a 1-phenyl-1-(3-(methoxycarbonyl)propyl) diazomethane. The synthesis by diazoalkane addition of cyclopropanyl-based fullerene derivatives (methanofullerenes) such as PCBM 3 may be accomplished by combining, with stirring, the diazocompound and fullerene $C_{60}$. This reaction scheme may also be used to prepare higher fullerene derivatives (Angew. Chem. 2003, 115, 3493-3497).

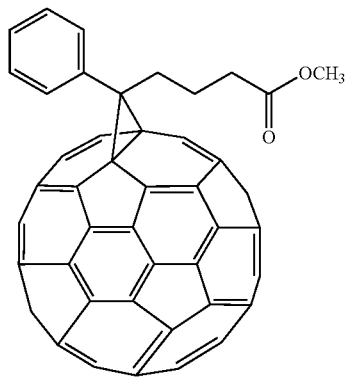

3

Figure 2:
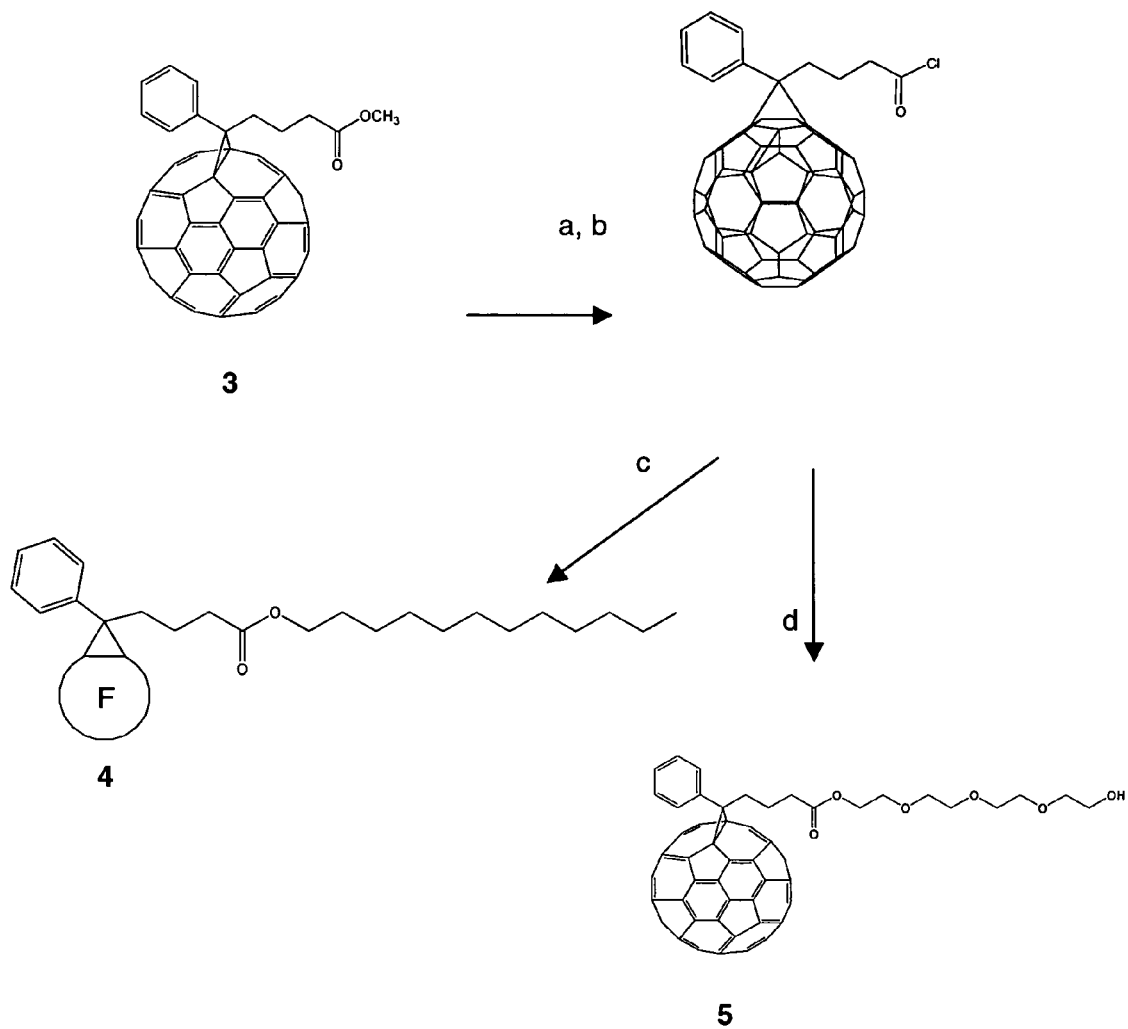
FIG. 2 illustrates a reaction scheme for the derivatization of a methanofullerene by acyl halide displacement, where F represents a fullerene cage structure.
Figure 3:
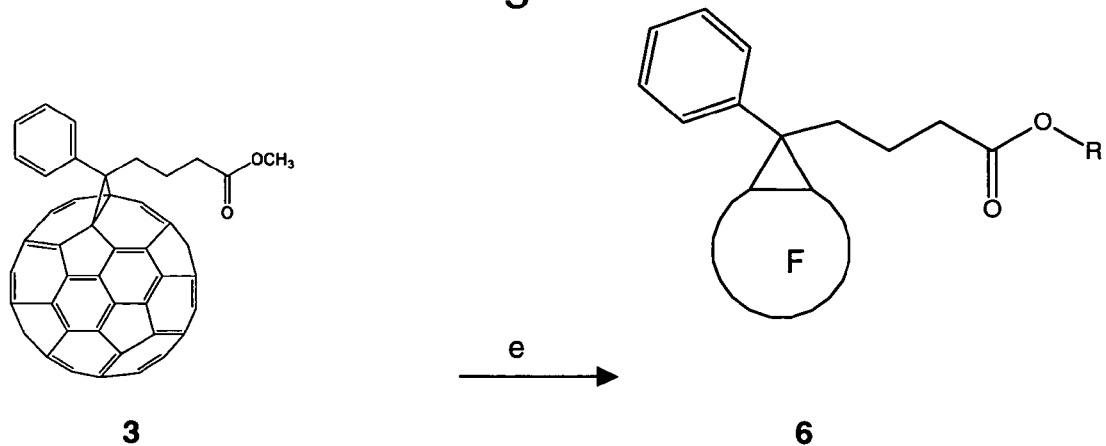
FIG. 3 illustrates a reaction scheme for the derivatization of a methanofullerene by transesterification from a PCBM molecule, where F represents a fullerene cage structure.
Figure 4A:
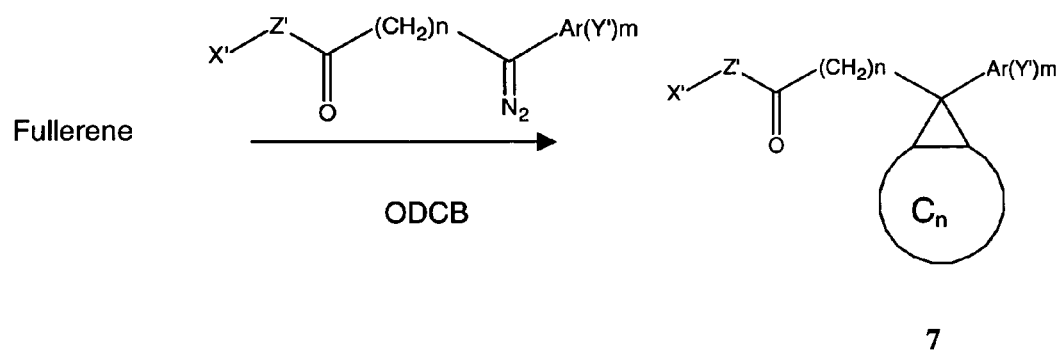
FIGS. 4A and 4B illustrate a reaction schemes for the direct formation of a derivatized methanofullerene according to one or more embodiments of the present invention.

The ester functional group (e.g., methyl ester in compound 3) allows for convenient synthesis of a large number of compounds, through displacement pathways illustrated in the reaction scheme of FIG. 2, or transesterifications illustrated in FIG. 3. The resultant compound 3', a higher fullerene analogue of PCBM, can be used as a chemical intermediate to synthesize an unlimited number of new fullerene derivatives having various functionalities. The compound 3' is first converted using reaction steps (a) [aqueous HCl/AcOH/1,2-dichlorobenzene] and (b) [$SOCl_2$/CS2] into the corresponding acid chloride 3a'. The acid chloride 3a' is then displaced by various groups to form a wide range of functionalized ester derivatives. Examples of this chemistry using $C_{60}$ can be found in the literature (for example, see Hummelen et al., J. Org. Chem. 1995, 60, 532), Thus, in FIG. 2, the methyl group is displaced to form a C12 alkyl ester 4 using reaction steps (c) [ROH/pyridine, where R=C12] or a polyethylene glycol ester 5 using reaction step (d) [ROH/pyridine, where R=$C_8H_{17}O_4$]. Alternatively, PCBM analogue 3' is transesterified using reaction step (e) [R—OH/$Bu_2SnO$/1,2-dichlorobenzene/heat] to obtain a transesterification compound 6. As an example, the synthesis of one higher fullerene derivative, [84]PCBM, is described below. This compound, [84] PCBM, being similar to PCBM (compound 3), is a suitable precursor to be converted into other molecules, such as by performing the modifications as described in FIGS. 2 and 3. Alternatively, diazoalkane addition chemistry can be used in a similar manner, but by forming the desired functionalized diazo compound before reaction with the fullerene molecule. See FIGS. 4A and 4B, where the appropriate diazo compound is selected to provide alkyl ester functionalized methanofullerenes 7 and aryl ester functionalized methanofullerenes 8.

The above methods allow for forming part (for example as shown in FIGS. 2 and 3) or all (for example as shown in FIGS.

4A and 4B) of the adduct added to the fullerene molecule of the following general form 1 all through diazoalkane addition chemistry,

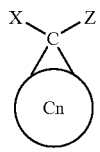

where the ring, $C_n$, is a fullerene selected from the group consisting of $C_{76}$, $C_{84}$, and $C_{90}$; where X and Z are the same or different, and where X or Z are independently selected from the group consisting of lipophilic moieties, hydrophilic moieties, amphiphilic moieties, free radical scavenging moieties.

A specific embodiment of compound 1 is shown below (compound 7), where Y' is any substituent on the aryl group; Ar is any aryl group; m greater than or equal to zero and indicates the total number of independent substituents Y' on the aryl group; n=1 to 20; Z' is any heteroatom (e.g., O, N, S); X' is any chemical group; and $C_n$ is a closed cage all-carbon molecule (fullerene) selected from the group consisting of $C_{76}$, $C_{84}$, and $C_{90}$.

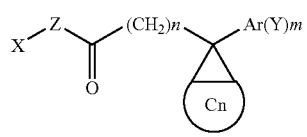

7

Aryl-substituted methanofullerenes are convenient for synthesis of the precursor diazoalkane, because common aromatic chemistry, such as Friedel Crafts acylation, can be used to prepare the diazo precursor. Also, it has been observed that aryl-substituted methanofullerenes are more amenable to photoisomerization from [5,6] fulleroids to [6,6] methano bridges.

Figure 4B:
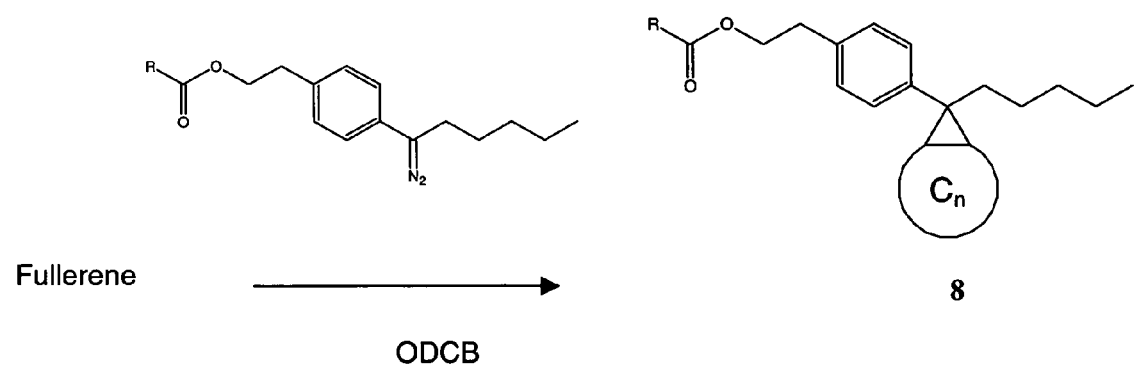

Another specific embodiment of compound 1 is shown below (compound 8), as shown in the product of FIG. 4B, where R is an alkyl group, for example a long chain, branched or linear, saturated or unsaturated carbon chain having more than 6 carbon atoms or more than 8 carbon atoms, or more than 12 carbon atoms, or more than 18 carbon atoms. Although a C5-alkyl group is shown for 8, alkyl groups having 1-20 carbons may be used.

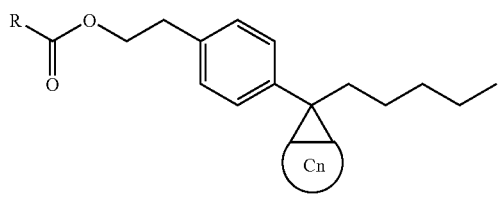

8

The molecules described above are useful for scavenging any type of radical, such as, but not limited to, radicals of biological importance, such as reactive oxygen species: —OH, —$O_2^-$, ROO—; $NO_x$ radicals; products of biological radical pathways such as fatty acid radicals and the products of biological radical scavengers reacting with radicals, such as tocopherol, ubiquinol, and ascorbyl radicals; auto-oxidation and products of auto-oxidation in polymer and other systems, such as food; radicals of environmental sources such as cigarette smoke and environmental combustion sources, such as automobile exhaust. Also, the present molecules may be used to scavenge radicals in radical polymerization reactions, to form co-polymers, enhance cross-linking, or to act as polymer stabilizers.

In various applications, it is desirable to target a fullerene to particular environments, e.g., for application in biological systems. For example, the target can be a dermal or other membrane surface or organ. The present invention provides a convenient means to synthesize new molecules with chemical functionalities for such targeting. Examples include but are not limited to the formation of lipophilic, hydrophilic, amphiphilic, or bio-site specific compounds, such as [monoclonal] antibodies, other proteins, {e.g., enzymes, protein hormones, membrane proteins, etc.}, steroids, coenzymes, co-factors, [oligo] DNA, RNA, enzyme inhibitors, enzyme substrates, specific cells or organs, tissues, and so on. For example, compound 4 is lipophilic, and could be used to target a fullerene to lipophilic environments, such as cell membranes, and/or to pass through cell membranes, and/or to penetrate the stratum corneum of the skin through the lipophilic phases of mammalian skin.

The higher fullerene free radical scavenging compound can be delivered to the target in a carrier vehicle. The free radical scavenging compounds may be administered to the target in solution, or in suspension. They may be prepared as a pharmaceutical composition using conventional forms for oral, topical, intramuscular, subcutaneous, and intravenous administration. Suitable carrier vehicles include those typically employed in the dermal application of pharmaceutical and cosmetic materials.

The effective dose of the higher fullerene free radical scavenging compound depends upon the manner of administration and condition of the biological system or patient to be treated. Methods of administration involve the step of bringing the higher fullerene free radical scavenging compound in a suitable carrier into contact with a target or a biological system or patient for treatment.

As another example, a more highly hydrophilic moiety could be attached as in compound 5 (or a poly-(ethylene glycol), a poly(ethylene oxide), mono-, di-, or poly-saccharides, or other hydrophilic moiety for enhanced hydrophilicity) for targeting of fullerenes to hydrophilic regions, such as in the hydrophilic phases of mammalian skin or to allow for biodistribution in the bloodstream, and/or absorption through the gastrointestinal tract. As yet another example, an amphiphilic molecule can be conveniently synthesized by attaching a hydrophilic moiety at the X position and a lipophilic moiety at the Z position in compound 1 or vice versa, or at any of the alternative points of substitution in compound 7.

Any constituent for targeting, including the hydro- and lipophilic moieties above, or any other such moieties, may be substituted at any of the substitution positions in compound 7, such as at X', Y', or Z'. Alternatively, other moieties important for biological targeting, such as but not limited to monoclonal antibodies may be substituted at X, Z, X', Y', or Z' in compounds 1 or 7.

Likewise, other chemical or physical functionalities may be added to a fullerene radical scavenging molecule by substitution at X, Z, X', Y', or Z', in the compounds described herein such as the following:

1. Enhanced solubility in media such as oils, alcohols, water, or aromatics, etc.;

2. Additional chemical reactivity, for example, the addition of other radical scavenging moieties, such as other antioxidants (e.g., carotenoids, flavinoids, anthocyanidins, lipoic acids, ubiquinoids, retinoids), for the formation of combination antioxidants in the form of molecular dyads,
3. Enhanced radical scavenging efficacy against a given radical, or to provide an effective multi-functional radical scavenger effective against different radicals (e.g., β-carotene, an efficient scavenger of singlet oxygen, but not of peroxyl, substituted at X, Z, X', Y', or Z', in compounds 1 or 7 to provide a single radical scavenging molecule effective against both singlet oxygen and peroxyl, against which fullerenes are effective);
4. For the formation of co-polymers to scavenge radicals in radical polymerization reactions, to form co-polymers, enhance cross-linking, or to act as polymer stabilizers;
5. The modification of physical properties, such as enhanced optical absorption;
6. To quench the singlet excited state of the fullerenes so that intersystem crossing to the excited triplet state of the fullerene does not occur and thus singlet oxygen is not generated.

The molecules of the instant invention can be used in compositions which contain these molecules, such as, but not limited to, salts of the molecules of the instant invention, e.g., pharmaceutically accepted salts and pharmaceutically accepted esters of the fullerene scavenging compounds described herein may be used; formulations containing molecules of the instant invention, including but not limited to compositions used in personal care, such as oil/water or water/oil emulsions; liposomal formulations, etc.; host-guest inclusions such as cyclodextrin complexes, etc.

The molecules described herein may be used in compositions with other reactive compounds, in particular in combination with other radical scavengers, such as tocopherols, ascorbates, ubiquinone, carotenoids, anthocyanidins, flavinoids, lipoic acids, etc. Fullerene molecules of the present invention may provide synergistic chemical effects, whereby the fullerene enhances or preserves the efficacy of one or more of the other substituent radical scavengers of the composition. Also, it is contemplated that the fullerenes described herein can be used to target another radical scavenger such as those mentioned here by chemical substitution of the radical scavenger at X, Z, X', Y', Z' in compounds described herein, to various environments, and/or preserve or enhance the efficacy in various environments. The higher fullerenes described herein may also be used in combination with other formulation agents such as stabilizers, surfactants, emulsifiers, preservative agents, UV absorbing agents, anti-inflammatory agents, or anti-microbial agents.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, the process as described above could easily be applied to other metazoans, including but not limited to humans, with the same results. Thus, the breadth and scope of the present invention should not be limited by any of the above-described exemplary embodiments, but should be defined only in accordance with the following claims appended hereto and their equivalents.

EXAMPLES

Example 1

Synthesis and Characterization of [84]PCBM

[84]PCBM was synthesized in a way analogous to the method for [60]PCBM and [70]PCBM (Hummelen et al., J. Org. Chem. 1995, 60, 532; Angew. Chem. 2003, 115, 3493-3497). The product was obtained by column chromatography in the following way: Elution with CS2 yielded unreacted C84. Then elution with cyclohexane: toluene (1:1 (v/v)) was started to obtain the mono-adduct. Both fractions were evaporated to dryness, redissolved in a minimal amount of ortho-dichlorobenzene and precipitated with MeOH. The resulting suspensions were centrifuged and the MeOH was decanted off. The resulting brown pellets were washed twice with MeOH, centrifuged and decanted. The obtained brown pellets were dried at 50° C. in vacuo for 2 days. Isolated yield: Recovered C84: 48.6 mg (4.8 10-2 mmol, 35%). Mono-adduct (mixture of isomers): 37.5 mg (3.12 10-2 mmol, 23%). IR (KBr); ν (cm-1): 3446 (m), 2942 (m), 1737 (s), 1628 (m), 1600 (w), 1517 (w), 1493 (w), 1455 (s), 1434 (s), 1384 (m), 1330 (m), 1261 (m), 1155 (m), 1056 (w), 1034 (s), 795 (s), 749 (s), 727 (w), 702 (s), 643 (s), 576 (m), 527 (w), 515 (w), 499 (m), 455 (w), 432 (w), 426 (w), 415 (w), 405 (w). 1H NMR (D2O, 400 MHz); δ (ppm): 8.0 (d, J=7.0 Hz, 2H), 7.89 (d, J=6.6 Hz, 2H), 7.58-7.41 (m, 3H), 7.26-7.23 (m, 3H), 3.65 (s, 3H), 3.64 (s, 3H), 3.63 (s, 3H), 3.47 (m, 2H), 3.27 (m, 2H), 3.09 (t, J=8.1 Hz, 2H), 2.54 (t, J=7.3 Hz, 2H), 2.51-2.46 (m, 2H), 2.28-2.22 (m, 2H). 13C NMR (CS2, 100 MHz); δ (ppm): 170.86, 170.80, 153.74, 151.57, 151.47, 151.29, 150.72, 149.95, 149.83, 143.57, 143.51, 143.09, 142.86, 142.56, 142.50, 142.16, 141.65, 141.45, 140.97, 140.90, 140.62, 140.57, 140.33, 140.31, 138.82, 138.78, 137.97, 137.93, 137.89, 137.47, 137.46, 137.33, 137.28, 137.23, 137.15, 137.01, 136.37, 135.77, 134.56, 134.50, 133.34, 133.07, 132.05, 131.94, 131.62, 130.02, 128.13, 128.08, 127.97, 127.84, 127.04, 64.75, 61.98, 61.74, 54.12, 50.83, 50.65, 50.62, 50.53, 37.23, 35.58, 35.05, 34.91, 34.78, 34.46, 33.88, 33.30, 33.26, 33.08, 33.03, 32.89, 29.75, 28:65, 26.37, 22.93, 22.84, 22.56, 21.86, 21.69, 21.37, 20.95, 20.69, 20.15

Example 2

Test of Radical Scavenging Efficiency

Figure 5:
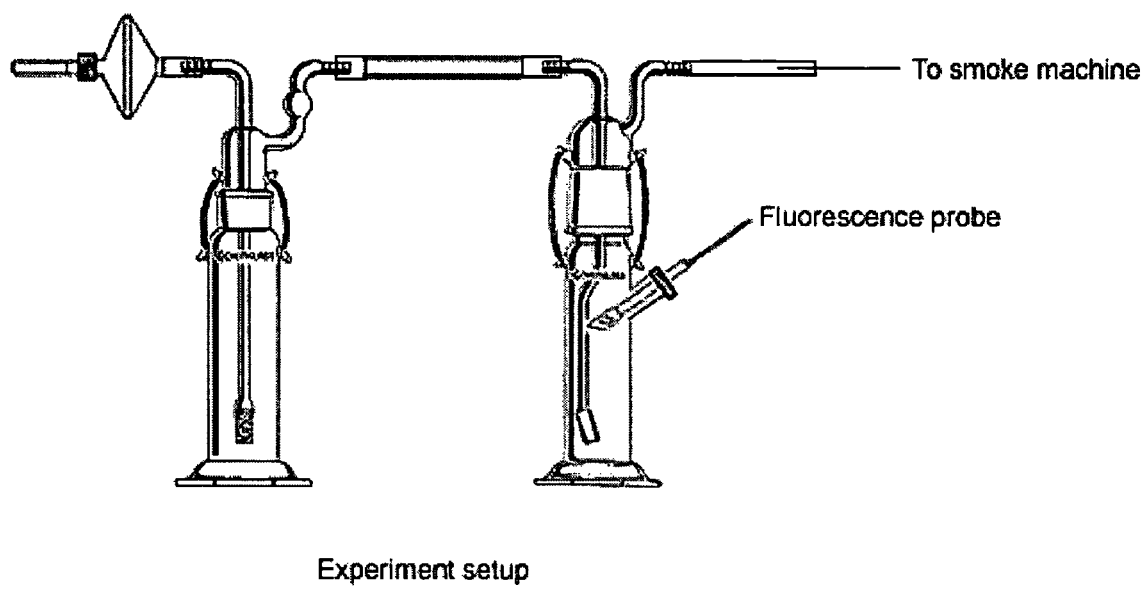
FIG. 5 is a schematic illustration of the apparatus used to determine free radical scavenging.
Figure 6A:
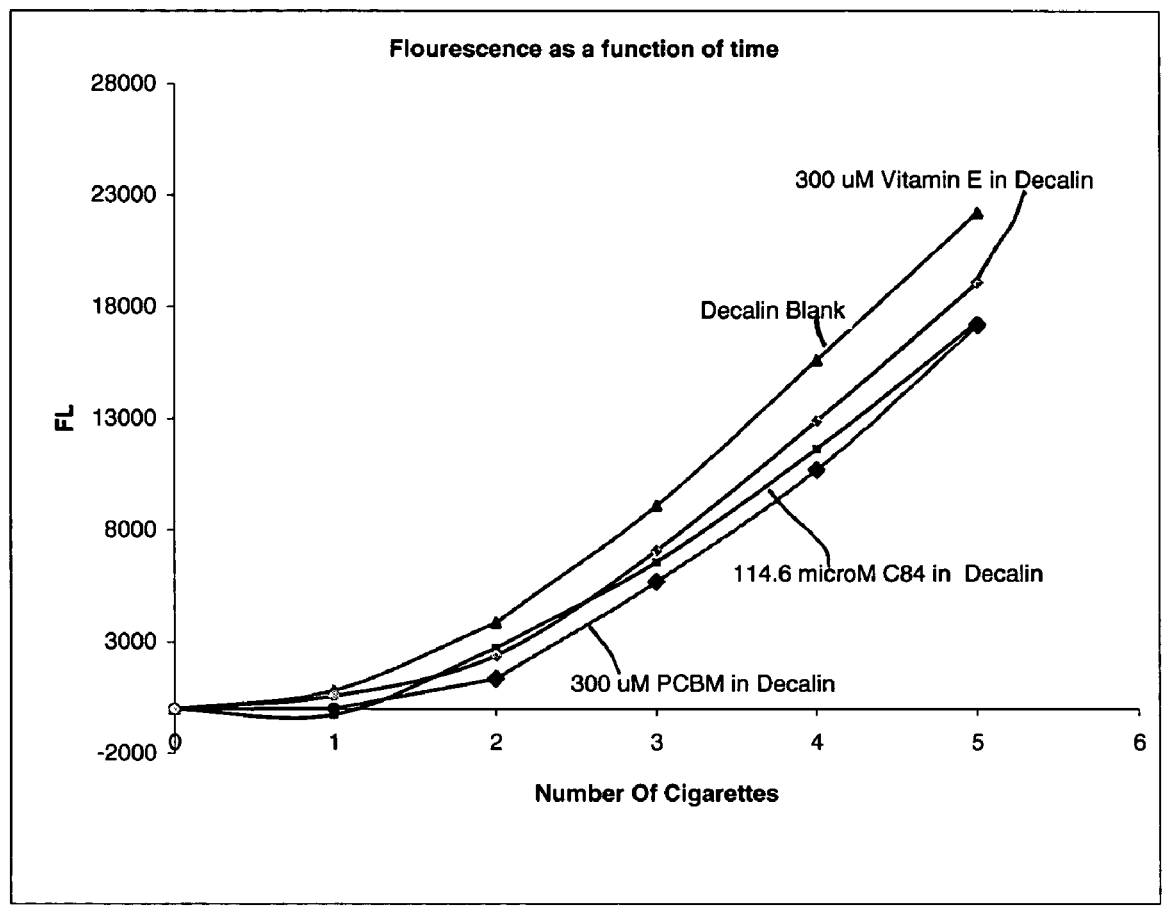
FIGS. 6A and 6B are plots of fluorescence resulting from the reaction of radicals contained in cigarette smoke with a dye which fluoresces upon reaction with radicals in the presence of various free radical scavenging molecules.

Tests were conducted to study the effectiveness of higher fullerenes against radicals present in cigarette smoke (predominantly peroxyl radical). The cigarette smoke was bubbled through a cylindrical, coarse glass frit into a solvent (decalin) in which radical scavengers were dissolved. The smoke then exited this solvent and was passed through a second flask, in which a fluorescent probe that fluoresces upon oxidation by radicals was used (Dihydrorhodamine 6G (DHR 6G), purchased from Molecular Probes). See FIG. 5. The variation of fluorescent signal corresponds directly to the radical content of the cigarette smoke, and thus a measure of the reduction of radicals by the radical scavenger is measured. Signals were measured every 10 seconds. FIG. 6A shows a comparison of the fluorescent signal measured under identical conditions for C84, and Vitamin E, a commonly used radical scavenger, and also known to be effective against peroxyl radical.

It can be seen that C84 clearly scavenges significantly more of the radicals present in the cigarette smoke than Vitamin E. Since peroxyl radicals are the major radical species present in cigarette smoke, molecules of the instant invention are also effective to prevent oxidative damage in biological systems, where peroxyl radical oxidation is a major pathway in lipid peroxidation. Hydroxyl radical is also present in cigarette smoke, and likewise is an important cause of oxidative stress in biological systems. Further, it is clearly seen that C84 scavenges radicals on a par with [60]PCBM, and even after 5 cigarettes gives the same radical scavenging effect at less than half the concentration of [60]PCBM, pointing to the possibility that C84 is a more efficient radical scavenger than C60.

Example 3

Comparison of Different Concentration Levels of Vitamin E

Figure 6B:
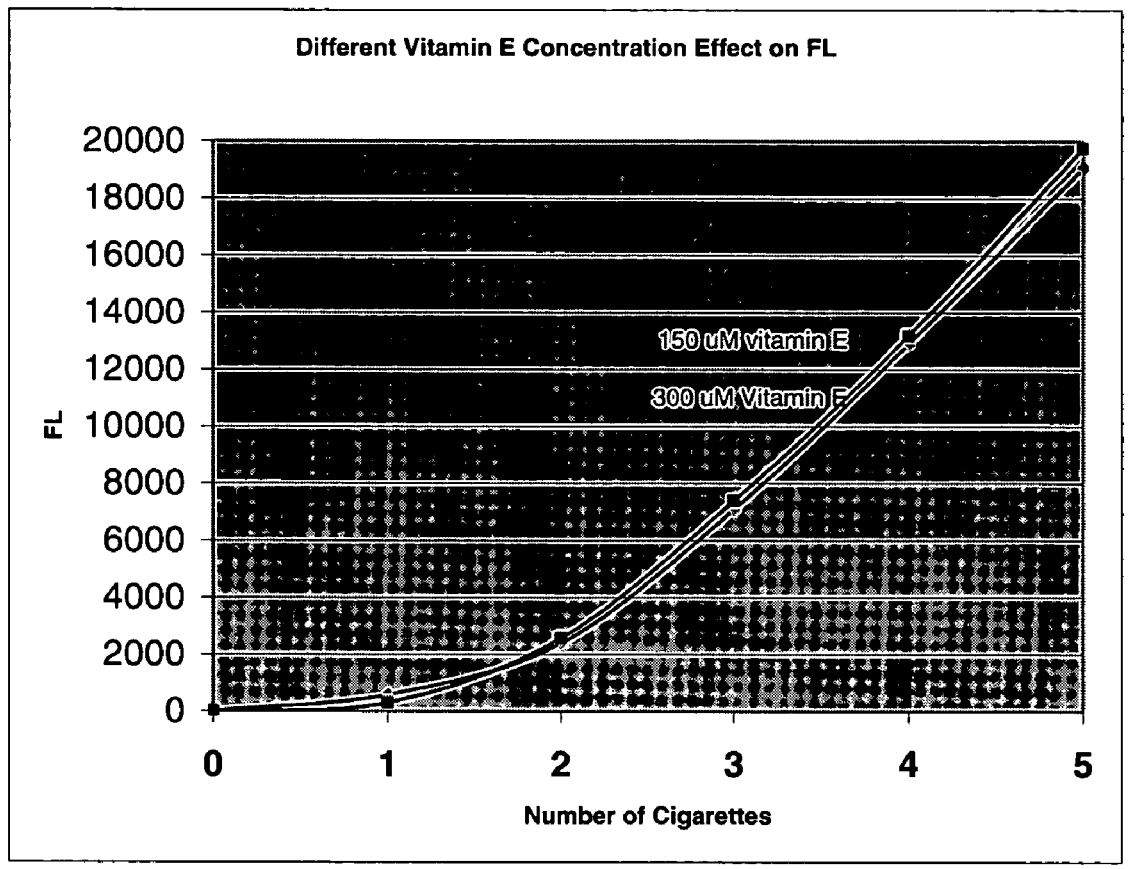

Tests were conducted to study the sensitivity of the test apparatus in Example 2 to varying concentrations of Vitamin E as a radical scavenger to scavenge radicals present in cigarette smoke (predominantly peroxyl radical). The cigarette smoke was bubbled through a cylindrical, coarse glass frit into a solvent (decalin) in which radical scavengers were dissolved. The smoke then exited this solvent and was passed through a second flask, in which a fluorescent probe that fluoresces upon oxidation by radicals was used (Dihydrorhodamine 6G (DHR 6G), purchased from Molecular Probes). See FIG. 5. The variation of fluorescent signal corresponds directly to the radical content of the cigarette smoke, and thus a measure of the reduction of radicals by the radical scavenger is measured. Signals were measured every 10 seconds. FIG. 6B shows a comparison of the fluorescent signal measured under identical conditions for 150 µM and 300 µM Vitamin E, a commonly used radical scavenger, and also known to be effective against peroxyl radical. It can be clearly seen that doubling the Vitamin E concentration from 150 µM to 300 µM gives a very small deflection. The difference in fluorescence signal between 115 µM C84 and 300 µM Vitamin E thus corresponds to a very large difference in radical scavenging efficiency.

Example 4

Comparison of Pro-Oxidant Activity of C60 and C84

Figure 7:
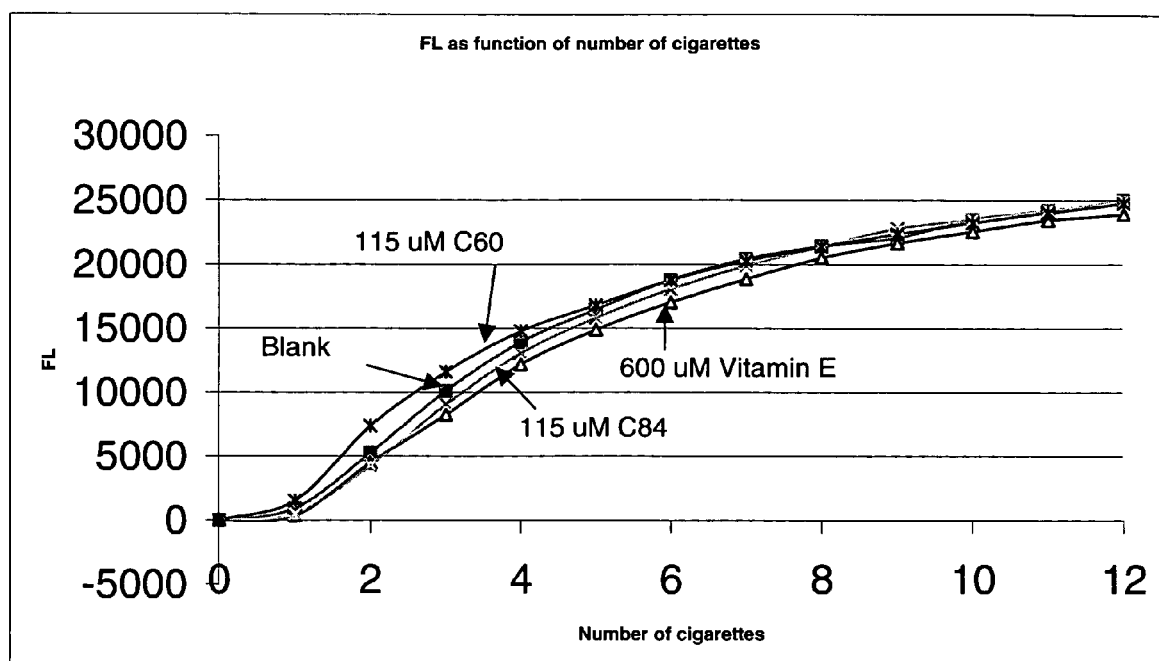
FIG. 7 is a plot of fluorescence comparing the signals measured under identical conditions for $C_{84}$, $C_{60}$ and Vitamin E.

Tests were conducted to study the effectiveness of higher fullerenes against radicals present in cigarette smoke (predominantly peroxyl radical). The cigarette smoke was bubbled through a medium glass frit, which gave much smaller bubbles and resultingly higher mass transfer of the smoke into a solvent (decalin) in which radical scavengers were dissolved. The smoke then exited this solvent and was passed through a second flask, in which a fluorescent probe that fluoresces upon oxidation by radicals was used (Dihydrorhodamine 6G (DHR 6G), purchased from Molecular Probes). See FIG. 5. The variation of fluorescent signal corresponds directly to the radical content of the cigarette smoke, and thus a measure of the reduction of radicals by the radical scavenger is measured. Signals were measured every 10 seconds. FIG. 7 shows a comparison of the fluorescent signal measured under identical conditions for C84, C60 and Vitamin E, a commonly used radical scavenger, and also known to be effective against peroxyl radical.

It can be seen that C60 creates more radicals than the blank, yet C84 scavenges radicals compared to the blank. This system is complex, in that many radical and non-radical species are present in the smoke, tetralin is likely present as an impurity in the decalin at higher concentrations than the fullerenes (tetralin may act as a H-donor radical scavenger), which may result in complex interactions between the fullerene radical scavengers, and transport of the smoke into the liquid may be a factor. Furthermore these tests were run in the absence of direct light, so singlet oxygen generation may not be a significant factor in the differences seen. Peroxyl radicals are the major radical species present in cigarette smoke, molecules of the instant invention are also effective to prevent oxidative damage in biological systems, where peroxyl radical oxidation is a major pathway in lipid peroxidation. Hydroxyl radical is also present in cigarette smoke, and likewise is an important cause of oxidative stress in biological systems.

What is claimed is:

1. A method of scavenging free radicals, the method comprising:
    administering one or more free radical scavenging compounds to a dermal substrate, and
    reducing the levels of free radicals without significantly increasing pro-oxidant activity while the one or more free radical scavenging compounds is on the dermal substrate and is exposed to irradiation,
    wherein the one or more free radical scavenging compounds are selected from the group consisting of $C_{84}$ fullerene and $C_{84}(Y)_m$, where $C_{84}$ is a fullerene, Y is a moiety attached, directly or indirectly, to the $C_{84}$ fullerene, where m is in the range of 1 to 30, and Y is selected from the group consisting of lipophilic moieties, hydrophilic moieties, amphiphilic moieties, free radical scavenging moieties, or bio-site specific moieties.

2. The method of claim 1, wherein the one or more free radical scavenging compounds do not significantly increase pro-oxidant activity due to triplet excited states of the one or more free radical scavenging compounds.

3. The method of claim 1, wherein the one or more free radical scavenging compounds do not generate singlet oxygen.

4. The method of claim 1, wherein Y comprises a lipophilic moiety and the lipophilic moiety is selected from the group consisting of alkanes, fatty acid, fatty esteramine, fatty alcohols, and fatty amine moieties.

5. The method of claim 1, wherein Y comprises a lipophilic moiety and the compound is capable of transport through or solubilization in lipid phases in a biological system.

6. The method of claim 1, wherein Y comprises a hydrophilic moiety.

7. The method of claim 6, wherein the hydrophilic moiety is selected from the group consisting of poly-(ethylene oxide)s, mono-, di- or poly-hydroxylated alkanes, mono-, di- or poly-hydroxylated cycloalkanes, amino alkanes, diamino alkanes, mono-, di-, or poly-saccharides, hydroxides, ammonium groups, alkylated ammonium groups, phosphates, alkylphosphates, sulfonates, and alkylsulfonates, phosphonium groups, carboxylate groups, sulfonic acid groups, iminium groups, imidine groups, and imidinium groups.

8. The method of claim 6, wherein Y comprises a hydrophilic moiety and the compound is capable of transport through or solubilization in aqueous phases in a biological system.

9. The method of claim 1, wherein Y comprises a chemical moiety that is independently effective as a free radical scavenger.

10. The method of claim 1, wherein Y comprises an amphiphilic moiety.

11. The method of claim 10, wherein the amphiphilic moiety is selected from the group consisting of polyethylene glycol, poly(ethylene oxide)s, propylene glycol, polypropylene glycol), hexylene glycol, diethylene glycol, propylene glycol n-alkanols, and glycol moieties.

12. The method of claim 1, wherein Y comprises a moiety which addresses a biological target such as [monoclonal] antibodies, proteins, enzymes, protein hormones, membrane proteins, steroids, coenzymes, co-factors, [oligo] DNA, RNA, enzyme inhibitors, enzyme substrates, specific cells or organs, tissues.

13. A method of scavenging free radicals, comprising:
administering to a dermal substrate a compound having the formula,

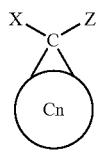

where the ring, $C_n$, is fullerene $C_{84}$; where X and Z are the same or different, and where X or Z are independently selected from the group consisting of lipophilic moieties, hydrophilic moieties, amphiphilic moieties, and free radical scavenging moieties; and
reducing the levels of free radicals without significantly increasing ro-oxidant activity while the compound is on the dermal substrate and is exposed to radiation.

14. The method of claim 13, wherein the compound does not significantly increase pro-oxidant activity due to triplet excited states of the compound.

15. The method of claim 13, wherein the lipophilic moiety is selected from the group consisting of alkanes, fatty acid, fatty esteramine, fatty alcohol, and fatty amine moieties.

16. The method of claim 15, wherein one or more of X and Z comprises a lipophilic moiety and the compound is capable of transport through or solubilization in lipid phases in a biological system.

17. The method of claim 13, wherein X or Z comprises a hydrophilic moiety.

18. The method of claim 16, wherein the hydrophilic moiety is selected from the group consisting of poly-(ethylene oxide)s, mono-, di- or poly-hydroxylated alkanes, mono-, di- or poly-hydroxylated cycloalkanes, amino alkanes, diamino alkanes, mono-, di-, or poly-saccharides, hydroxides, ammonium groups, alkylated ammonium groups, phosphates, alkylphosphates, sulfonates, and alkylsulfonates, phosphonium groups, carboxylate groups, sulfonic acid groups, iminium groups, imidine groups, and imidinium groups.

19. The method of claim 17, wherein one or more of X and Z comprises a hydrophilic moiety and the compound is capable of transport through or solubilization in aqueous phases in a biological system.

20. The method of claim 13, one or more of X and Z comprises a chemical moiety that is independently effective as a free radical scavenger.

21. The method of claim 13, wherein one or more of X and Z comprises an amphiphilic moiety.

22. The method of claim 21, wherein the amphiphilic compound is selected from the group consisting of polyethylene glycol, poly(ethylene oxide)s, propylene glycol, polypropylene glycol), hexylene glycol, diethylene glycol, propylene glycol n-alkanols, and glycol moieties.

23. The method of claim 13, wherein one or more of X and Z is a non-electron withdrawing group.

24. The method of claim 23, wherein the non-electron withdrawing group is selected from the group consisting of alkyls, cyclic alkyls, substituted alkyls, alkylaryls, alkyl ethers, alkylaryl ethers, alkyl thioethers, alkylaryl thioethers, alkyl esters, alkylaryl esters, alkyl thioesters, alkylaryl thioesters, alkyl amides, alkylaryl amides, alkyl amines, alkylaryl amines, alkyl anhydrides, alkylaryl anhydrides, alkyl carbonates (or carboxylic acids), alkylaryl carbonates, arylalkyls, aryl ethers, arylalkyl ethers, aryl thioethers, arylalkyl thioethers, aryl esters, arylalkyl esters, aryl thioesters, arylalkyl thioesters, aryl amides, arylalkyl amides, aryl amines, arylalkyl amines, aryl anhydrides, arylalkyl anhydrides, aryl carbonates (or carboxylic acids) and arylalkyl carbonates.

25. The method of claim 1 or 13, further comprising:
exposing the target to at least one additional radical scavenging compound.

26. The method of claim 1 or 13, wherein the compound further comprises:
an additive selected to enhance or preserve the efficacy of the compound.

* * * * *